United States Patent [19]

Engel et al.

[11] 4,283,405
[45] Aug. 11, 1981

[54] DITHIENYLPIPERIDINES, PHARMACEUTICAL COMPOSITIONS THEREOF, AND METHOD OF USE THEREOF

[75] Inventors: Jurgen Engel, Alzenau; Axel Kleemann, Hanau; Fritz Stroman, Offenbach; Klaus Thiemer, Hanau, all of Fed. Rep. of Germany

[73] Assignee: Degussa Aktiengesellschaft, Frankfurt, Fed. Rep. of Germany

[21] Appl. No.: 112,099

[22] Filed: Jan. 14, 1980

[30] Foreign Application Priority Data

Jan. 17, 1979 [GB] United Kingdom ............... 7901659

[51] Int. Cl.³ .................. A61K 311/38; C07D 409/14; A61K 31/445
[52] U.S. Cl. .................................. 424/267; 546/213; 546/212; 542/430; 542/432
[58] Field of Search ................. 546/212, 213; 424/267

[56] References Cited

U.S. PATENT DOCUMENTS 2,739,968  3/1956  Sperber et al. ................... 546/212
5,175,088  11/1979  Kleeman et al. ................. 549/59

FOREIGN PATENT DOCUMENTS 2128808  11/1975  Fed. Rep. of Germany ........... 546/313
2800536  7/1978  Fed. Rep. of Germany ........... 549/59

OTHER PUBLICATIONS

Waldvogel, "Helv. Chim. Acta" vol. 59 pp. 866–877 (1979).

Olofson et al., "Tetrahedron Letters" (1977) pp. 1567–1970.
Fodor et al., "J. Org. Chem." vol. 39, No. 11 (1974) pp. 1507–1516.

*Primary Examiner*—Robert T. Bond
*Attorney, Agent, or Firm*—Cushman, Darby & Cushman

[57] ABSTRACT

There are prepared compounds of the formula

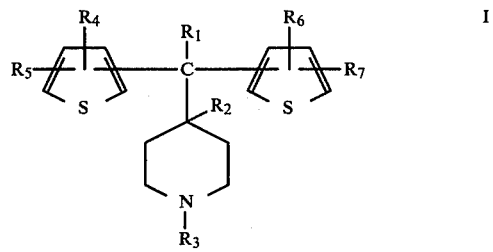

wherein $R_1$ and $R_2$ are hydrogen or together represent a second bond between the carbon atom carrying $R_1$ and $R_2$, $R_1$ also can be a hydroxy group, $R_3$ is hydrogen, a $C_3$–$C_8$ cycloalkyl group or a $C_1$–$C_{20}$ alkyl group, which optionally can also contain one or two hydroxy groups and the groups $R_4$, $R_5$, $R_6$ and $R_7$ are the same or different and are hydrogen, $C_1$–$C_6$-alkyl groups or halogen atoms, their N-oxide, their quaternary salts and their acid addition salts. There are also described processes for their production. The compounds possess especially an antischemic and blood pressure increasing activity.

30 Claims, No Drawings

DITHIENYLPIPERIDINES, PHARMACEUTICAL COMPOSITIONS THEREOF, AND METHOD OF USE THEREOF

BACKGROUND OF THE INVENTION

There are known through Sperber U.S. Pat. No. 2,739,968 compounds having spasmolytic, analgesic and antihistamine activity having the following formula:

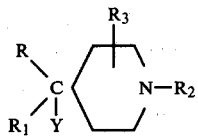

wherein for example $R_2$ is a methyl or also an ethyl group, R and $R_1$ are two thienyl -(2)- groups, $R_3$ is hydrogen and Y is hydrogen or a hydroxy group or also together with the piperidine ring form a double bond and Y is hydrogen or a hydroxy group or also together with the piperidine ring can form a double bond.

The German Offenlegungsschrift No. 2128808 is directed to compounds of the general formula:

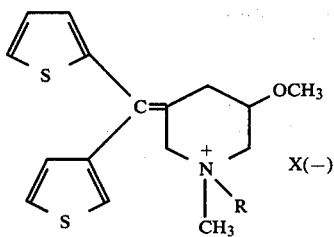

where R is a lower alkyl group and X is an anionic residue of a pharmaceutically acceptable acid. There is likewise stated for these compounds a spasmolytic activity which is comparable to that of atropine sulfate.

SUMMARY OF THE INVENTION

There are prepared compounds of the formula

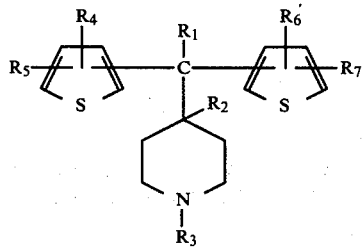

wherein $R_1$ and $R_2$ are hydrogen or together represent a second bond between the carbon atom carrying $R_1$ and $R_2$, $R_1$ also can be a hydroxy group, $R_3$ is hydrogen, a $C_3$–$C_8$ cycloalkyl group or a $C_1$–$C_{20}$ alkyl group, which optionally can also contain one or two hydroxy groups and the groups $R_4$, $R_5$, $R_6$ and $R_7$ are the same or different and are hydrogen, $C_1$–$C_6$-alkyl groups or halogen atoms, their N-oxide, their quaternary salts and their acid addition salts. There are also described processes for their production. The compounds possess especially an antischemic and blood pressure increasing activity.

In the case where $R_3$ is an unsubstituted $C_1$–$C_6$-alkyl group there must be present at least one thienyl-(3)-group.

The alkyl groups in the compound of formula I can be straight chain or branched. In case $R_4$, $R_5$, $R_6$ and/or $R_7$ are alkyl groups, these particularly have 1 to 4 carbon atoms, preferably they are methyl. In case $R_4$, $R_5$, $R_6$ and/or $R_7$ are halogen, these are for example fluorine, chlorine or bromine. In case $R_3$ is an alkyl group which contains a hydroxy group this hydroxy group is preferably located in the 2-position (the 1-position of the alkyl group is the linking position with the nitrogen atom of the piperidine ring).

In additional to the compounds mentioned in the specific examples illustrative of other novel compounds and/or compounds which can be used for pharmaceutical purposes within the invention include 4-[di-3-(2,5-dimethyl)-thienyl-methylene]-N-methyl-piperidine 4-[di-3-(2,5-dibutyl)-thienyl-methylene]-N-methyl-pyridine, 4-[3-thienyl-(2,5-dihexyl-3-thienyl)-methylene]-N-methyl-pyridine, 4-[di-3-(2-bromo)-thienyl-methylene]-N-methyl-piperidine, 4-[di-3-(2-fluoro)-thienyl-methylene]-N-methyl-piperidine, 4-(di-3-thienyl-methylene)-N-cyclopropyl-piperidine, 4-(di-2-thienyl-methylene)-N-cyclopropyl-piperidine, 4-(di-2-thienyl-methyl)-N-cyclopropyl-piperidine, 4-di-3-thienyl-(N-cyclohexyl-4-piperidyl)-carbinol, 4-(di-3-thienyl-methylene)-N-cycloctyl-piperidine, 4-(di-3-thienyl-methyl)-N-butyl-piperidine, 4-(di-3-thienyl-methyl)-N-sec.butyl-piperidine, 4-[di-3-(2,5-dimethyl)-thienyl-methyl]-N-methyl-piperidine, 4-[di-3-(2,5-dimethyl)-thienyl-methyl]-N-(2-hydroxyethyl)-piperidine, 4-[di-2-(2,5-dimethyl)-thienyl-methyl]-N-(2-hydroxypropyl)-piperidine, 4-(di-2-thienyl-methyl)-N-(2-hydroxyethyl)-piperidine, 4-[3-thienyl-(2-methyl-3-thienyl)-methylene-N-methyl-piperidine, 4-[3-thienyl-(2,5-dichloro-3-thienyl)-methylene]-N-methyl-piperidine 4-[3-thienyl-(2-chloro-3-thienyl)-methyl]-N-(2-hydroxyethyl)-piperidine, 4-[2-thienyl-(2-chloro-3-thienyl)-methylene]-N-methyl pyridine, 4-[di-3-(2,5-dichloro)-thienyl-methylene]-N-methyl-piperidine.

4-(di-30thienyl-methylene)-N-eicosanyl-piperidine, 4-(di-3-thienyl-methylene)-N-(2-hydroxyeicosanyl)-piperidine, 4-[di-3-(2-methyl-5-chloro)-thienyl-methylene]-N-methyl-piperidine.

The compounds of the invention are pharmacodynamically active and as indicated above have an antiischemic as well as blood pressure increasing activity. Furthermore they effect an increase of the peripheral blood flow and frequently lower the heart frequency (bradycardia). Several compounds, particularly those where $R_3$ is a hydroxyalkyl group, for example the 2-hydroxyethyl group, also have an analgesic activity. The invention is thus based, at least in part on making available compounds which have favorable pharmacodynamic properties which are useful as medicines.

The compounds of the present invention of formula I are prepared by reacting (a) a compound of the formula

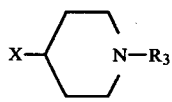

II which also can contain three conjugated ring double bonds where $R_3$ is as defined above ($R_3$ is eliminated in case a pyridine ring is present) and X stands for either (A) The group —COZ where Z is a halogen atom, e.g. chlorine, bromine, fluorine or iodine, or a $C_1$–$C_6$-alkoxy group, e.g., methoxy, ethoxy, propoxy, butoxy or hexoxy or a thienyl group which in a given case is substituted once or twice by halogen atoms and/or $C_1$–$C_6$-alkyl groups or (B) Lithium or the group —MgHal where Hal is chlorine, bromine or iodine, or in the case of (A) with a compound

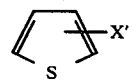

III wherein X' is lithium or the group —Mg Hal and the thienyl group also can be substituted once or twice by halogen atoms and/or $C_1$–$C_6$-alkyl groups or in the case of (B) is reacted with a compound of the formula

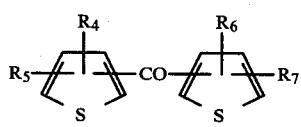

IV and the compounds obtained in a given case treated with a reducing agent and/or dehydrating agent and/or alkylated through the group $R_3$ and/or converted into the N-oxide or (b) starting from a compound of formula I and in case $R_1$ is the hydroxy group and $R_2$ is hydrogen either treating this with a dehydrating and/or reducing agent and-/or exchanging the $R_3$ group for another group within the definition of $R_3$ and in a given case converting the compound obtained into the N-oxide.

Process (a)

The process is suitably carried out in a temperature range between $-100°$ and $+150°$ C., preferably $-75°$ to $+100°$ C. or up to $+50°$ C. In case there is used a thienyl-(3)-metal compound (especially thienyl lithium) or a thienyl-(3)-metal Grignard compound there are preferably employed low temperatures, especially below $-50°$ C. in an inert medium. In such cases it is advantageous to carry out the reaction temperature between $-70°$ and $-80°$ C. The temperature between $-70°$ and $-80°$ C. is especially true for thienyl-(3)-metal compounds. As solvents there are suitable for example saturated aliphatic symmetrical and unsymmetrical dialkyl ethers with alkyl groups of for example 1–6 carbon atoms, e.g. dimethyl ether, diethyl ether, dipropyl ether, diisopropyl ether, propyl butyl ether, dibutyl ether or dihexyl ether, $C_1$–$C_6$ alkyl ethers of cycloIk-anols and alkyl substituted cycloalkanols wherein the cycloalkanol ring in each case has 3, 4, 5 or 6 carbon atoms, e.g. methyl cyclohexyl ether, methyl cyclopentyl ether or ethyl cyclohexyl ether; saturated $C_5$–$C_7$-cycloaliphatic hydrocarbons wherein the latter preferably can be substituted one to three times by $C_1$–$C_4$ alkyl groups e.g. hexane, pentane, octane, nonane, cyclohexane, cyclopentane, cycloheptane, methyl cyclohexane, methyl cyclopentane, ethyl cyclohexane, butyl cyclohexane, dimethyl cyclohexane or trimethyl cyclohexane; tetrahydrofuran; benzene; benzene substituted by $C_1$–$C_3$-alkyl groups, e.g. toluene, xylene, ethyl benzene or propyl benzene. Especially preferred are ethers and aliphatic or cycloaliphatic hydrocarbons which are liquid in the range between $-80°$ and $+20°$ C.

The stated solvents can also be used in mixtures. For example a solvent mixture can be used which consists of a staturate ether and benzene substituted by $C_1$–$C_3$-alkyl groups. These kind of solvent mixtures are described for example in German Offenlegungsschrift No. 2,800,536 and related Kleemann U.S. Pat. No. 4,175,088, the entire disclosure of which is hereby incorporated by reference and relied upon.

A corresponding excess of metal organic compound is always necessary if the other reactants contain active hydrogen (amino, hydroxy groups, salt). However, it is generally frequently recommended to use an excess of metal organic compound since better yields are produced through this.

In case Z in the group —COZ (formula II) is a halogen atom it is preferably chlorine, bromine or iodine.

Starting materials of the formula

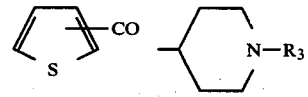

wherein the thienyl group also can be substituted by halogen or lower alkyl groups can be obtained for example through reaction of the corresponding thienyl lithium or thienyl Grignard compound with the compound

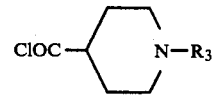

or through reaction of the corresponding thienyl cyanide or thienyl carbonyl chloride with the compound

(Hal = chlorine or bromine, in case a pyridine ring is present $R_3$ is eliminated)

in a solvent or suspension agent as is customary for Grignard reactions (for example lower saturated aliphatic ethers, e.g. those set forth above, benzene, methyl substituted benzene) at a temperature between $-80°$ and $+100°$ C.

Furthermore there can also be obtained such starting materials from a compound

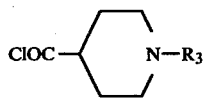

and the corresponding thiophene in the presence of AlCl₃ according to the Friedel-Crafts process.

Starting materials of formula IV can be obtained for example through Friedel-Crafts acylation of a compound

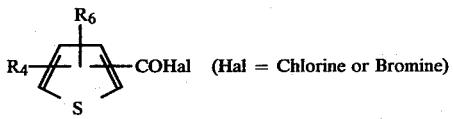

with a compound

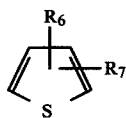

in the presence of AlCl₃ in a solvent such as dichloroethane, nitromethane at a temperature between 0° and +100° C.

Furthermore they can be obtained through Grignard reaction of a compound

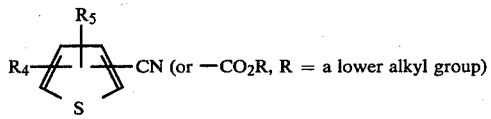

with a compound

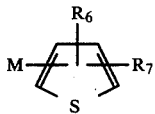

wherein M is lithium or magnesium chloride or magnesium bromide in a solvent or suspension agent such as is customary for Grignard reactions at a temperature between −80° and +100° C.

Starting materials of formula II wherein X is the group —MgHal can be obtained for example from compounds of the formula II wherein X is chlorine, bromine or iodine through customary Grignard—or lithium—Grignard reaction using Mg or metallic lithium in the customary solvents for this (for example tetrahydrofurane, lower aliphatic ethers, lower alkyl benzenes) at a temperature between 20°–120° C. In a given case the Grignard reaction must be initiated by means of iodine plus dibromomethane.

The splitting off of water from compound of formula I wherein $R_1$ is the hydroxy group and $R_2$ is hydrogen (the remaining symbols can have the stated meanings) is carried out suitably at higher temperatures, for example in a temperature range of 20°–150° C. Preferably there are used solvents as for example glacial acetic acid, benzene, dioxane, lower aliphatic alcohols, e.g. methyl alcohol, ethyl alcohol, propyl alcohol, isopropyl alcohol.

As agents for splitting off water there can be used for example mineral acids such as sulfuric acid or hydrohalic acids, e.g. hydrochloric acid or hydrobromic acid; organic acids such as oxalic acid, formic acid; thionyl chloride; zinc chloride; tin chloride; boron trifluoride; potassium hydrogen sulfate; aluminum chloride; phosphorus pentoxide; aluminum oxide; acid chloride, e.g. acetyl chloride; red phosphorus plus iodine in the presence of water.

Frequently a partial splitting off of water takes place already in the working up of the reaction products obtained through reaction of compounds of formula II with compounds of formula III or IV.

The reduction of compounds of formula I wherein $R_1$ and $R_2$ form the double bond or $R_1$ is the hydroxy group and $R_2$ is hydrogen as well as the products of the process which contain three double bonds in the piperidine ring (the remaining symbols having the stated meaning) can be carried out for example with hydrogen in the presence of hydrogenation catalysts, suitably in a solvent such as an alcohol, e.g. isopropyl alcohol, ethyl alcohol or methyl alcohol, dioxane, tetrahydrofurane, benzene, acetic acid, ethyl acetate. As hydrogenation catalyst there are particularly employed noble metal catalysts such as palladium, platinum, etc. or sulfidic catalysts such as palladium sulfide, platinum sulfide, rhenium heptasulfide and the like. The catalysts can be used with or without carrier. As carriers there are suited for example barium sulfate, aluminum oxide, etc. The hydrogenation is suitably carried out at a temperature between 20° and 100° C. at normal pressure or elevated pressure up to for example 100 bar. A pressure between 2 and 20 bar is preferred.

Furthermore there can be used as reducing agent nascent hydrogen, for example metallic sodium in a lower alcohol (ethanol for example) with or without addition of water, sodium in liquid ammonia, sodium amalgam in the presence of an acid such as dilute hydrochloric acid, dilute sulfuric acid or acetic acid. In this case there is generally employed room temperatures or elevated temperature up to about 150° C.

Furthermore, for example it is also possible to employ electrolytic reduction or reduction with other hydrogen supplying agents such as complex metal hydrides, for example alkali-borohydrides, e.g. sodium borohydride, lithium alanate, sodium-bis-(2-methoxy-ethoxy)-aluminum hydride in the presence of hydrogenation catalysts.

With the reduction, especially with catalytic hydrogenation (Pd-CaCO₃) or also electrolytic reduction, in a given case there can be removed halogen atoms in the 2,5-positions on the thiophene ring. A selective splitting off of halogen atoms in the thiophene ring is possible for example with zinc/glacial acetic acid.

If there are present as starting material compounds of formula I wherein $R_1$ is the hydroxy group and $R_2$ is hydrogen then there is frequently recommended the simultaneous addition of dehydrating materials. As dehydrating agent there can be used for example mineral acids such as sulfuric acid or hydrohalic acids, e.g. hydrochloric acid or hydrobromic acid, organic acids such as oxalic acid or formic acid; thionyl chloride; aluminum chloride; zinc chloride; tin chloride; boron trifluoride; potassium hydrogen sulfate; aluminum oxide; phosphorus pentoxide; acid chlorides, e.g. acetyl chloride or benzoyl chloride. Especially there is used as the reducing agent nascent hydrogen in acid medium.

The reduction can be carried out in solution or suspension. As solvents there can be employed for example those already mentioned.

In case the product of the process contains three conjugated double bonds in the piperidine ring (pyridine ring) above all there are considered for the hydrogenation of the nucleus of this pyridine ring, platinum, rhodium and ruthenium catalysts ($PtO_2$; rhodium/carbon, ruthenium dioxide) at a temperature between 20° and 50° C. and normal pressure to 10 bar. As solvents there are suited for this particularly lower alcohols, e.g. methanol, ethanol or ispropanol, dioxane, tetrahydrofurane, glacial acetic acid, alcoholic hydrochloric acid. Frequently it is suitable to hydrogenate the corresponding hydrochloride. A hydrogenation of the pyridine ring, however, for example is also possible with alkali metals (e.g. sodium) in lower alcohols (e.g. ethanol) at 20° to 150° C.

The conversion of the compounds of formula I into the corresponding N-oxide can be carried out for example in inert solvents, such as chloroform or other chlorohydrocarbons, benzene, toluene, acetone or ethyl acetate with hydrogen peroxide, a conventional aliphatic or aromatic peracid (peracetic acid, perbenzoic acid, m-chloroperbenzoic acid) or other mono substitution products of hydrogen peroxide such as alkyl peroxides (for example tert. butyl peroxide) at a temperature between 0° and 150° C., preferably 0° to 100° C.

Process (b)

Compounds of formula I wherein $R_1$ is the hydroxy group and $R_2$ is hydrogen and the remaining symbols have the stated meanings can be converted by treatment with dehydrating agents into compounds of formula I wherein $R_1$ and $R_2$ together form a second bond between the carbon atoms carrying the substituents $R_1$ and $R_2$. This dehydration takes place in the manner already stated above.

Compounds of formula I wherein $R_1$ and $R_2$ form the second bond between the carbon atoms carrying the substituents $R_1$ and $R_2$ or wherein $R_1$ is the hydroxy group and $R_2$ is hydrogen and the remaining symbols can have the stated meaning are converted by treatment with reducing agents into such compounds in which $R_1$ and $R_2$ are hydrogen. The conditions for this reduction have already been given above.

The conversion into N-oxide likewise takes place in the manner already stated above.

Compounds of general formula I wherein $R_3$ is hydrogen and the remaining symbols have the given meaning can be obtained by reaction with a compound of the formula:

$$R_3—Hal \qquad V$$

wherein $R_3$ has the stated meaning except hydrogen and Hal is a chlorine bromine or iodine atom or together with the next but one $CH_2$- group of $R_3$ also can form an ethylene oxide ring.

This reaction can be carried out with or without solvent at a temperature between 20° to 200° C., preferably 50° to 150° C. As solvents of dispersing agents there can be used for example, aromatic hydrocarbons such as for example, benzene, toluene, xylene, aliphatic ketones as, for example, acetone, methyl ethyl ketone, halogenated hydrocarbons such as for example chloroform, carbon tetrachloride, chlorobenzene, methylene chloride, aliphatic ethers such as for example dibutyl ether; cyclic ethers as for example tetrahydrofurane, dioxane, sulfoxides as for example dimethyl sulfoxide; tertiary acid amides as for example dimethyl formamide, N-methyl pyrrolidone; aliphatic alcohols such as methanol, ethanol, isopropanol, amyl alcohol, tert. butanol; cycloaliphatic hydrocarbons such as cyclohexane and the like. There can also be used aqueous mixtures of the solvents mentioned. Frequently the process is operated at the reflux temperature of the solvent of dispersing agent used. Generally the reactants are reacted in molar amounts. In a given case the reaction can also be carried out in the presence of acid binding agents such as alkali carbonates (potash, sodium carbonate), alkali hydroxides (e.g. NaOH or KOH) or tert. amines (for example triethyl amine). The latter is especially true if the corresponding halide is employed.

The compounds of formula I for example can also be employed in the form of a metal salt, especially alkali salt (sodium or potassium salt for example). This is particularly true if the other reactant is a halide.

In carrying out the reaction as the ethylene oxide starting material instead of the ethylene oxide compound there can also be employed the corresponding halohydrin or a mixture of the two compounds (synthesis-crude product).

Compounds of general formula I wherein $R_3$ is a lower alkyl group (especially the methyl or ethyl group) can be transposed in known manner for this purpose through dealkylation into compounds wherein $R_3$ is hydrogen (see for this purpose Houben Weyl, Methoden der Organischen Chemie, Vol. XI/I, pages 976–990 (1957); Olofson Tetrahedron Letters No. 18, pages 1567 to 1570 (1977); Folor J. Org. Chem. Vol. 39, pages 1507–1516 (1974); Waldvogel, Helvetica Chemica Acta, Vol. 59, pages 866 to 877 (1976).

For example this dealkylation can be carried out with chloroformic acid esters such as ethyl chloroformate, vinyl chloroformate, phenyl chloroformate in an inert solvent such as aromatic hydrocarbons (toluene, xylene, benzene), lower aliphatic halohydrocarbons such as 1,2-dichloroethane between $-50°$ to $+100°$ C. and subsequently there is carried out acidic or basic saponification with for example alcoholic alkali (KOH/butan) or alcoholic mineral acids, (HCl, HBr, $H_2SO_4$) at a temperature between 50° and 150° C.

The compounds of the invention are generally obtained as racemates. The optically active antipodes are obtained either through the use of optically active starting materials or through the splitting of the racemate by way of the salts of optically active acids as for example, L-(+)-tararic acid, D-(−)-tartaric acid, (+)-O,O'-dibenzoyl-D-tartaric acid, (−)-O,O'-dibenzoyl-L-tartaric acid, (−)-O,O'-di-p-toluoyl-L-tartaric acid, (+)-O,O'-di-p-toluoyl-D-tartaric acid, (+)-camphor-10-sulfonic acid and others.

The compounds of general formula I can be converted into the salts by known methods. As anions for these salts there can be employed the known and therapeutically acceptable acid residues. Examples of such acids are sulfuric acid, phosphoric acid, hydrohalic acid, e.g. hydrochloric acid or hydrobromic acid, ethylenediamine tetraacetic acid, sulfamic acid, benzenesulfonic acid, p-toluenesulfonic acid, camphorsulfonic acid, methanesulfonic acid, guaiazulenesulfonic acid, maleic acid, fumaric acid, succinic acid, tartaric acid, lactic acid, ascorbic acid, glycolic acid, salicyclic acid, acetic acid, propionic acid, gluconic acid, benzoic acid, citric acid, acetaminoacetic acid and hydroxyethane sulfonic acid.

The free bases can be produced again from the salts of the compounds in customary manner, for example by treating a solution in an organic medium, such as alcohols (e.g. methanol) with sodium carbonate or sodium hydroxide.

The conversion into the quaternary salts takes place by reaction of the corresponding secondary or tertiary amino compounds with lower alkyl halides (1 to 6 carbon atoms), chlorides, bromides, iodides, e.g. methyl chloride, methyl bromide, methyl iodide, hexyl chloride, hexyl bromide, hexyl iodide, ethyl chloride, ethyl iodide, isopropyl bromide, butyl chloride, butyl bromide, butyl iodide) in a solvent or suspension agent such as aromatic hydrocarbons (e.g. benzene, toluene, xylene), halogenated aliphatic hydrocarbons ($CHCl_3$, $CH_2Cl_2$), saturated aliphatic ethers, e.g. diethyl ether, cyclic ethers (e.g. dioxane), dimethyl sulfate at a temperature between 0° and 100° C.

The compounds of the invention are suitable for the production of pharmaceutical compositions. The pharmaceutical compositions or medicaments can contain one or more of the compounds of the invention or even mixtures of them with other pharmaceutically active compounds. For the production of pharmaceutical preparations there can be used the usual pharmaceutical carriers and adjuvants.

As stated, the compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared with the usual pharmaceutical excipients, assistants, carriers, and diluents.

As carriers and assistants, for example, are those recommended in the following literature as adjuvants for pharmacy, cosmetic and related fields such as in Ullmann's Encyklopädie technischen Chemie, Volume 4, (1953), pages 1 to 39; Journal of Pharmaceutical Sciences 52 (1963), pages 918 et seq., H. v. Czetsch-Lindenwald, Hilfstoffe fur Pharmazie and angrenzende Gebiete; Phar. Ind. 2 (1961), pages 72 et seq., D. H. P. Fiedler, Lexicon der Hilfstoffe fur Pharmazie, Kosmetik und angrenzende Gegiete, Cantor kg. Aulendorf i. Württ. (1971).

Examples of such materials include gelatin, natural sugars such as sucrose or lactose, lecithin, pectin, starch (for example cornstarch), alginic acid, tylose (methyl cellulose), talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example methyl hydroxypropyl cellulose, methyl cellulose, hydroxyethyl cellulose), stearates, e.g. methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example peanut oil, castor oil, olive oil, sesame oil, cottonseed oil, corn oil, wheat germ oil, sunflower seed oil, cod-liver oil), mono- di- and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, penaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atoms alkanols) or polyhyrdic alcohols such as glycols, glycerine, diethylene glycol, pentaerthritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols, can in a given case also be etherified, benzyl benzoate, dioxolane, glycerine formal, tetrahydrofurfuryl alcohol, polyglycol ethers with 1 to 12 carbon atoms alcohols, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and clygeryl acetate, partial esters of glycerine, e.g., monoacetic diacetin, glyceryl monostearate, glyceryl distearate, glyceryl monopalmitate, paraffins and the like.

In the production of the preparations there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxide-condensation products of fatty alcohols, alkylphenols or fatty acids. As used therein polyoxyethylated means that the materials in questions contain polyoxyethylene chains whose degree of polymerization generally is between 2 and 40, particularly between 10 and 20.

Such polyoxyethylated materials for example can be obtained by reaction of hydroxyl group containing compounds (for example mono- or diglycerides) or unsaturated compounds such as, for example, those containing the oleic acid radical with ethylene oxide (for example 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195).

Furthermore, there can be added preservatives, stabilizers, buffers, for example, calcium hydrogen phosphate, colloidal aluminum hydroxide, taste correctives, antioxidants and complex formers (for example ethylene diamine tetracetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium metabisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antiioxidant activity of tocopherol. As preservatives there can be used for example sorbic acid, p-hydroxybenzoic acid esters (for example lower alkyl esters such as the methyl ester and the ethyl ester), benzoic acid, sodium benzoate, trichloroisobutyl alcohol, phenol cresol, benzethonium chloride and formalin, derivatives).

The pharmacological and galenical treatment of the compounds of the invention takes place according to the usual standard method. For example, the acitve material or materials and assistants or carriers are well mixed by stirring or homogenization (for example by means of a colloid mill or ball mill), wherein the operation is generally carried out at temperatures between 20° and 80° C., preferably 20° to 50° C.

The application of active material or drug can take place on the skin or mucous membrane or internally, for example orally, enterally, pulmonally, rectally, intravenously, nasally, vaginally, lingually, intraarterially, intracardially, intramuscularly, intraperitoneally, subcutaneously or intracutaneously.

The addition of other medicines is also possible or favorable.

The compounds of the invention with narcotized, thoroacotomized dogs in which a local, limited disturbance of the blood supply is produced by narrowing of a coronary atery branch display a good anti anginosis activity which can be deleted exactly as to extent and duration with the help of epicardial electrocardiogram signals (EKG signals). The determination of this activity takes place for example according to the method of Skekeres, et al, J. Pharmacol exper. Ther. Vol 196, page 15, et seq. (1976) with the following change: the stenosis was set on the coronary vessel itself. The activity of the substance is shown in a reduction of the changes caused by the stenosis in the characteristic segment of the EKG signal which is carried off from the surface of the heart. For example in the above mentioned test method after a dosage of 3 mg/kg dog intravenously the change in the electrocardiogram (EKG) is reduced in the eschemic region around 62%. This therapeutic effect is combined with a reduction in frequency and moderate increase in blood pressure.

This antiagninosis activity is comparable with the known medicine, nitroglycerine.

The lowest clearly antianginosis effective dosage in the above stated animal tests, for example, is 1 mg/kg orally, 1 mg/kg sublingually and 0.1 mg/kg intravenously.

As the general dosage range for the antianginosis (animal experiments as above), there can be used, for example:

1 to 50 mg/kg orally, especially 3 to 20 mg/kg; 1 to 50 mg.kg sublingually, especially 3 to 20 mg/kg, 0.1 to 20 mg/kg intravenously, especially 1 to 10 mg/kg.

The compounds of the invention are indicated for:

agina pectoris, heart infarct, tachycardia rhythm disturbances.

The pharmaceutical preparations can for example, contain between 10 and 500 mg of the active component or components of the invention.

The compounds can be delivered in the form of tablets, capsules, pills, dragees, plugs, salves, jellies, creams, dusts, aerosols, or in liquid form. As liquid form there can be used, for example, oily or alcoholic or aqueous solutions as well as suspensions and emulsions. The preferred forms of use are tablets which for example contain between 50 and 500 mg or solutions which for example contain between 1 and 5% of active material.

In individual doses, the amount of active components of the invention can be used for example in an amount of:

(a) in oral dispensation between 200 and 500 mg;

(b) in parenteral dispensation (for example, intravenously, intramuscularly) between 100 and 300 mg;

(c) in rectal or vaginal application between 200 and 500 mg; and (d) for local application to the skin and mucous membranes (for example in the form of solutions, lotions, emulsions, salves, etc.) between 1 and 5%.

For example, there is recommended the use of 1 to 3 tablets containing 100 to 200 mg of active ingredients 3 times daily or for example, intravenously the injection 1 to 3 times daily of a 2 to 10 ml ampoule containing 50 to 100 mg of active substance. In oral dispensation the minimum daily dosage for example is 200 mg; the maximum daily dosage in oral administration should not be over 1.5 gram.

The dosages in each case are based on the free base.

The acute toxicity of the compounds of the invention in the mouse (expressed by the $LD_{50}$ mg/kg method of Miller and Tainter, Proc. Soc. Exper. Biol. an Med. 57 (1944), pages 261 et seq.) in oral application is between 300 mg/kg and 1000 mg/kg.

The drugs can be used in human medicine, in veterinary medicine as well as in agriculture alone or in admixture with other pharmacologically active materials. The compounds can be used for example to treat dogs, cats, horses and cattle.

The method can comprise, consist essentially of or consist of the steps set forth with materials shown. The compositions can comprise, consist essentially of or consist of the materials set forth.

Unless otherwise indicated all parts and percentages are by weight.

The present invention is illustrated by the following examples.

DESCRIPTION OF THE PREFERRED EMBODIMENTS

EXAMPLE 1

(Di-3-Thienyl)-(N-methyl-4-piperidyl)-carbinol

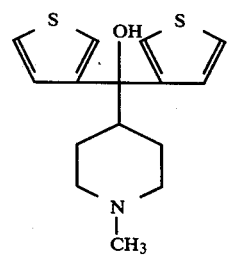

(a) 4.86 grams (0.2 gram atom) of magnesium was covered with absolute tetrahydrofurane and treated with a particle of iodine and 0.5 ml of dibromoethane.

As soon as the reaction had started there was dropped in within 15 minutes 26.5 grams (0.198 mole) of 4-chloro-N-methyl piperidine dissolved in 30 ml of absolute tetrahydrofurane. Subsequently the mixture was heated for 2 hours under reflux and then diluted with 120 ml of absolute tetrahydrofurane. To this there was added at room temperature 19.4 grams (0.1 mole) of β-dithienyl ketone in small portions.

Subsequently the mixture was allowed to react further for 2 hours at the boiling temperatures. The reaction mixture was poured on ice/ammonium chloride (250 grams/25 grams) for hydrolysis. The organic phase was separated off, the aqueous phase shaken several times with chloroform. After drying and distilling off the solvent in a vacuum the desired product was isolated. Through dry column chromatography on silica gel (elution agent: ether/methanol=90%/10% by volume). To form the salt the free base obtained was dissolved in ethanol and treated with the quimolar amount of maleic acid, likewise dissolved in ethanol. The maleate was recrystallized from ethanol. M.P. of the maleate: 189°–191° C., Yield: 25% (based on the β-dithienyl ketone.

(b) To a mixture consisting of 350 ml of diisopropyl ether and 200 ml of butyl lithium (20% solution in hexane) there were dropped in at −75° C. 63,5 grams (0.38 mole) of 3-bromothiophene dissolved in 100 ml of diisopropyl ether. After the addition took place the mixture was further stirred for 2 hours before there were added dropwise at −75° C. a solution of 33 grams (0.19 mole) of N-methyl-4-piperidine carboxylic acid ethyl ester in 50 ml of diisopropyl ether. In all operations the reaction temperature should not exceed −70° C. The hydrolysis took place through the addition of 250 ml of water. The product was extracted several times with chloroform. After the customary drying the solution was concentrated and cooled. The carbinol which crystallized out was filtered off with suction and dried and without further purification added for the dehydration (see Example 2). Yield: 73%.

EXAMPLE 2

4-(Di-3-thienyl-methylene)-N-methyl-piperidine

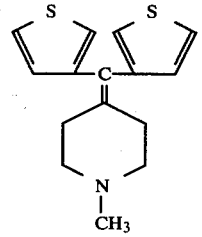

14 grams (0.048 mole) of (di-3-thienyl)-N-methyl-4-piperidyl)-carbinol (crude product) were dissolved in 200 ml of methanol, treated with 20 ml of 8 N isopropanolic hydrochloric acid and heated for 1 hour. The solvent was removed under reduced pressure and the hydrochloride obtained recrystallized from isopropanol.

M.P. of the hydrochloride 230° C.; Yield: 79%.

The starting carbinol was obtained in a manner analogous to Example 1 (b).

EXAMPLE 3

4-[3-Thienyl-(2,5-dimethyl-3-thienyl)-methylene]-N-methyl-piperidine

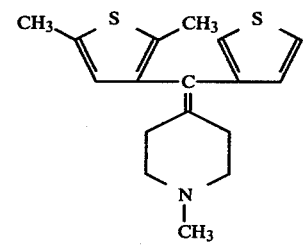

4 grams of (2,5-dimethyl-3-thienyl)-(N-methyl-4-piperidyl)-3-thienyl)-carbinol were dehydrated in 50 ml of methanol with 10 ml of 8 N isopropanolic HCl in a manner analogous to Example 2.

For purification first the base was set free from the oily hydrochloride obtained using ammonia. This was isolated by dry column chromatography on silica gel (elution agent: ether/methanol 95%/5%, dissolved in acetone and treated with the equimolar amounts of oxalic acid. The oxalate obtained was recrystallized from ethyl acetate/ethanol. M.P. of the oxalate 155°–157° C.; Yield: 56%.

The starting carbinol was obtained in a manner analogous to Example 1 (a), from 12.2 grams (0.055) mole) of (2,5-dimethyl-3-thienyl)-3-thienyl ketone, 14.7 grams (0.11 mole) of 4-chloro-N-methyl-piperidine and 2.67 grams (0.11 gram atom, of magnesium.

EXAMPLE 4

4-(Di-3-thienyl-methylene)-N-cyclohexyl-piperidine

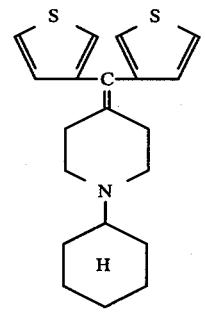

5 grams of (di-3-thienyl)-N-cyclohexyl-4-piperidyl)-carbinol in 50 ml of methanol were dehydrated with 10 ml of 8 N isopropanolic HCl in a manner analogous to Example 2 and worked up. The hydrochloride was recrystallized from isopropanol.

M.P. of the hydrochloride 232° C.; Yield: 41%

The starting carbinol was produced in a manner analogous to Example 1(b).

EXAMPLE 5

4-(Di-3-thienylmethylene)-piperidine

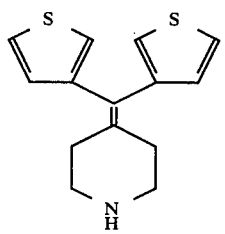

The solution of 122 grams (0.443 mole) of 4-(di-3-thienylmethylene)-N-methyl-piperidine in 400 ml of toluene at 80° C. was dropped into a mixture of 100 grams (0.886 mole) of ethyl chloroformate and 200 ml of toluene. After ending the addition the reaction mixture was stirred for 3 hours more at 80° C. and concentrated by distillation of the solvent in a vacuum. Hereby the 4-(di-3-thienyl-methylene)-N-carbethoxy piperidine crystallized out and was recrystallized from isopropanol. (Yield: 98%; M.P. 109°–111° C.).

A mixture of 163 grams (0.484 mole) of this carbethoxy compound, 120 grams (2.2 moles) of potassium hydroxide and 1200 ml of n-butanol were boiled under reflux until after the thin layer chromatographic controlling the starting compound was completely reacted. The butanol was removed in a vacuum, the residue treated with water and shaked several times with methylene chloride. The salt formation took place with maleic acid in acetone as the solvent. Yield: 68%, M.P. of the maleate 173° to 174° C.

EXAMPLE 6

4-(Di-2-thienyl-methylene)-N-(2-hydroxy-ethyl)-piperidine

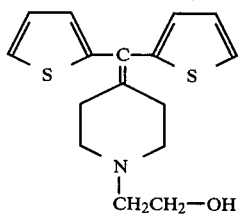

6.8 grams (0.026 mole) of 4-(di-2-thienyl-methylene)-piperidine and 12.6 grams (0.156 mole) of 2-chloroethanol were dissolved in 100 ml of xylene and heated under reflux in the presence of 21.6 grams (0.156 mole) of potassium carbonate for 10 hours. After the addition of water, separation of the organic phase, repeated extraction of the aqueous phase with chloroform, purification and drying of the organic phases the solvent was distilled off in a vacuum and the hydrochloride obtained using isopropanolic hydrochloric acid and acetone as solvent. The recrystallization took place from isopropanol, M.P. of the hydrochloride 196° C.; Yield: 63%.

The production of the thienyl starting material was carried out in a manner analogous to Example 5.

EXAMPLE 7

4-(Di-3-thienyl-methylene)-N-(2-hydroxy-ethyl)-piperidine

This compound was produced in a manner analogous to Example 6 from 6.8 grams of 4-(di-3-thienyl-methylene)-piperidine and 12.6 grams of 2-chloroethanol. M.P. of the hydrochloride 170°–171° C. (from isopropanol) Yield: 48%.

EXAMPLE 8

4-(Di-3-thienyl-methylene)-N-[2-hydroxy-propyl-(1)]-piperidine

This compound was produced in a manner analogous to Example 6 from 6.8 grams of 4-(di-3-thienyl-methylene)-piperidine and 4.9 grams of 1-chloro-2-hydroxy-propane. M.P. of the hydrochloride (from isopropanol) 209° C.; Yield: 22%.

EXAMPLE 9

4-[Di-2-thienyl-methylene]-N-[2,3-dihydroxy-propyl-(1)]-piperidine

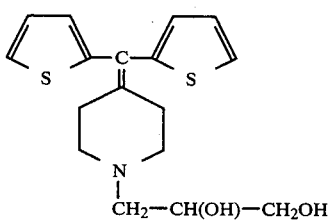

10 grams (0.038 mole) of 4(di-2-thienyl-methylene)-piperidine and 5.6 grams (0.076 mole) of glycidol were dissolved in 50 ml of ethanol and heated under reflux for 8 hours. Subsequently the solvent was removed and the desired glycidyl compound isolated by dry column chromatography on silica gel (elution agent: Chloroform). For further purification there was produced the hydrochloride and it was recrystallized twice from isopropanol. M.P. of the hydrochloride 141°–143° C.; Yield: 33%.

In a manner analogous to Example 9 there were produced the compounds set forth in Table 1 of the following formula:

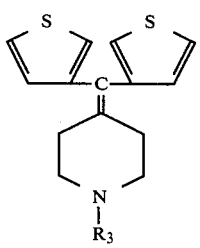

In each case there were reacted 0.038 mole of 4-(di-3-thienyl-methylene)-piperidine with 0.076 mole of the glycide corresponding to the alcohol $R_3OH$.

TABLE 1

| Example | R₃ | Yield | M.P. (°C.) | Recrystallization Agent |
|---|---|---|---|---|
| 10 | —CH₂—CH(OH)—CH₂—OH | 15% | 130–132° (hydrochloride) | Isopropanol |
| 11* | —CH₂—CH(OH)—(CH₂)—₃CH₃ | 31% | 69–71° (Base) | Isopropanol |
| 12* | —CH₂—CH(OH)—(CH₂)₉CH₃ | 76% | 82–83° (Base) | Ethanol |
| 13* | —CH₂—CH(OH)—(CH₂)₁₅CH₃ | 78% | 92–93° (Base) | Ethanol |

*In place of ethanol there was used isopropanol as the solvent. Besides the column chromatographic purification can be eliminated.

EXAMPLE 14

4-(Di-3-thienyl-methylene)-N-dimethyl-piperidiumiodide

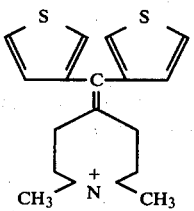

30 grams (0.11 mole) of 4-(di-3-thienyl-methylene)-N-methyl-piperidine in 200 ml of ether were treated with 28.4 grams (0.20 mole) of methyl iodide. After standing for several hours in the refrigerator the precipitated crystals were filtered off with suction and recrystallized from methanol/water. M.P. 272° C.; Yield: 56%.

EXAMPLE 15

4-(Di-3-thienyl-methylene)-N-methyl-piperidine-oxide

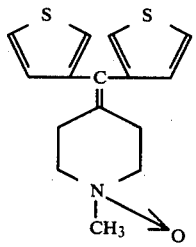

5.5 grams (0.02 mole) of 4-(di-3-thienyl-methylene)-N-methyl-piperidine were dissolved in 50 ml of methanol and treated with 7.2 grams of 30% hydrogen peroxide dropwise with ice cooling and left at room temperature for 8 days. Excess hydrogen peroxide was destroyed by the addition of Pt-carbon. After the filtering and removal of the solvent at room temperature the amineoxide was crystallized in ethyl acetate. M.P. 92°–96° C.; Yield: 77%.

EXAMPLE 16

4-(Di-3-thienyl-methyl)-N-methyl-piperidine

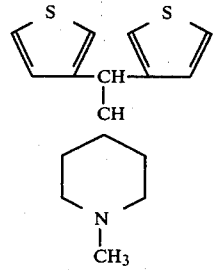

9.5 grams (0.03 mole) of 4-(di-3-thienyl-methylene)-N-methyl-piperidine hydrochloride were dissolved in 270 ml of methanol and hydrogenated in the presence of 9.5 grams of PdBaSO₄ (9.25% Pd) at 65° C. and 5 bar. The purification was carried out by dry column chromatography on silica gel (elution agent: chloroform/methanol=95%/5% by volume) and recrystallization from chloroform/petroleum ether. M.P. of the hydrochloride 251°–253° C.; Yield: 11%.

EXAMPLES OF PHARMACEUTICAL PREPARATIONS

EXAMPLE 17

Tablets 8 kg of active material (compound of Example 6) were mixed with 5 kg of lactose and 3 kg of microcrystalline cellulose and granulated in conventional manner with a solution of 0.3 kg of polyvinyl pyrrolidone in 1.2 kg of water.

After mixing in 3.45 kg of microcrystalline cellulose, 2 kg of corn starch, 0.05 kg of highly dispersed silica as well as 0.2 kg of magnesium stearate there were molded tablets having a weight of 220 mg, a diameter of 9 mm and a radius of curvature of 13.5 mm. Half the tablets carried 5–7 kg (Heberlin-hardness tester). Each tablet contained 80 mg of active material.

EXAMPLE 18

Ampoules 400 grams of active material (compound of Example 7) were dissolved in a mixture of 4 kg of 1,2-propylene glycol and 15 kg of water for injection purposes, the total solution filled up with water for injection purpose to 20 liters and filtered. After filling the solution in ampoules to 2 ml the product was sterilized in the customary manner at 120° C., 1 bar for 20 minutes. One ampoule contains 40 mg of active material.

The entire disclosure of British priority application No. 7901659 is hereby incorporated by reference.

What is claimed is:

1. A compound having the formula

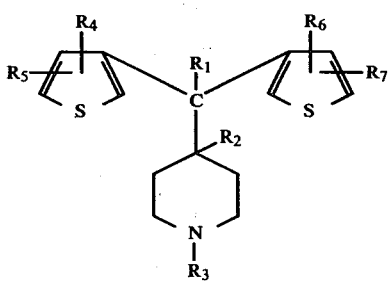

where $R_1$ is hydrogen or hydroxy, $R_2$ is hydrogen or $R_1$ and $R_2$ together represent a second bond between the carbon atoms carrying $R_1$ and $R_2$, $R_3$ is a $C_3$-$C_8$ cycloalkyl group or a $C_1$-$C_{20}$ alkyl group containing one or two hydroxy groups and the groups $R_4$, $R_5$, $R_6$ and $R_7$ are hydrogen, $C_1$-$C_6$-alkyl groups or halogen atoms, an N-oxide thereof, a quaternary salt thereof with a compound of the formula $R_8Y$ where $R_8$ is alkyl of 1 to 20 carbon atoms and Y is chlorine, bromine or iodine or an acid addition salt thereof with a therapeutically acceptable acid.

2. A compound according to claim 1 which is a compound of said formula, an N-oxide thereof or an acid addition salt thereof with a therapeutically acceptable acid.

3. A compound according to claim 2 which is a compound of said formula or an N-oxide thereof.

4. A compound according to claim 3 which is a compound of said formula.

5. A compound according to claim 1 where $R_3$ is a $C_3$-$C_8$-cycloalkyl group.

6. A compound according to claim 1 wherein $R_3$ is a $C_1$-$C_{20}$ alkyl group containing 1 to 2 hydroxy groups.

7. A compound according to claim 6 wherein $R_3$ has a hydroxy group on the carbon atom adjacent to the carbon atom attached to the piperidine ring.

8. A compound according to claim 7 having a single hydroxy group in $R_3$.

9. A compound according to claim 7 wherein $R_3$ is 2,3-dihydroxypropyl.

10. A compound according to claim 1 in the form of a quaternary salt thereof.

11. A compound according to claim 1 which is an N-oxide.

12. A compound according to claim 1 where $R_1$ is OH.

13. A compound according to claim 1 where $R_1$ is H.

14. A compound according to claim 1 wherein $R_1$ and $R_2$ together represent a second bond between the carbon atoms carrying $R_1$ and $R_2$.

15. A medicament having antianginosis activity which comprises a compound as claimed in claim 1 in an amount effective to prevent anginosis together with a pharmacologically acceptable carrier.

16. A method of preventing anginosis in a mammal comprising administering to the mammal an effective amount of a compound of claim 1 to prevent anginosis.

17. A method according to claim 16 wherein the compound is administered orally.

18. A method according to claim 16 wherein the compound is administered intravenously.

19. A method according to claim 16 wherein $R_1$ is OH.

20. A method according to claim 16 wherein $R_1$ is H.

21. A method according to claim 16 wherein $R_1$ and $R_2$ together represent a second bond between the carbon atoms carrying $R_1$ and $R_2$.

22. A method according to claim 16 wherein $R_3$ is a $C_3$-$C_8$-cycloalkyl group.

23. A method according to claim 16 wherein $R_3$ is a $C_1$-$C_{20}$ alkyl group containing 1 to 2 hydroxy groups.

24. A method according to claim 23 wherein $R_3$ has a hydroxy group on the carbon atom adjacent to the carbon atom attached to the piperidine ring.

25. A method according to claim 24 having a single hydroxy group in $R_3$.

26. A method according to claim 24 wherein $R_3$ is 2,3-dihydroxypropyl.

27. A method according to claim 16 wherein the compound is an N-oxide.

28. A method according to claim 16 where $R_1$ is OH.

29. A method according to claim 16 where $R_1$ is H.

30. A method according to claim 16 where $R_1$ and $R_2$ together represent a second bond between the carbon atoms carrying $R_1$ and $R_2$.

* * * * *